DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 24, 1970

880 O.G. 1162

T880,007

PREPARATION OF PURIFIED AROMATIC ACID

Olden E. Paris, Wilmington, Del., and Robert H. Sullivan, Woodbury, N.J., assignors to E. I. du Pont de Nemours and Company, Wilmington, Del., a corporation of Delaware

Filed Jan. 15, 1970, Ser. No. 3,234
Int. Cl. C07c *51/42*
U.S. Cl. 260—525
No Drawing. 7 Pages Specification

Purified aromatic acid is prepared from an aqueous solution of an alkali metal salt of the acid which contains reducible impurities, wherein the alkali metal is selected from the group consisting of sodium, potassium, rubidium and cesium, by reducing the impurities by catalytic hydrogenation, followed by acidifying the solution to precipitate the purified acid. The process is particularly useful for preparing purified terephthalic acid, especially where the reducible impurities are salts of aldehyde acids such as para-formylbenzoic acid. The reducible impurities are hydrogenated by contacting the aqueous solution with hydrogen in the presence of a hydrogenation catalyst at a pressure of from 0 to about 100, preferably 25 to 50 p.s.i.g., and at a temperature of about from 25 to 100° C., preferably 40 to 75° C. Any of the known hydrogenation catalysts can be used, but preferred catalysts are nickel/kieselguhr, cobalt/kieselguhr, nickel/aluminum oxide, active copper chromite, Raney nickel and chromium-promoted Raney nickel, with chromium-promoted Raney nickel being especially preferred. The amount of catalyst should be about from 0.5 to 3, preferably 1 to 2, percent by weight based on the amount of aromatic acid salt. The hydrogenation should generally be continued for about from 30 to 90 minutes, with a slight excess of hydrogen over stoichiometric quantities being used to insure complete reduction of the impurities.